United States Patent [19]

Ono et al.

[11] Patent Number: 5,229,270
[45] Date of Patent: Jul. 20, 1993

[54] REAGENT FOR THE DETERMINATION OF CHLORINE ION

[75] Inventors: Toshihiro Ono; Junichi Taniguchi, both of Kanagawa, Japan

[73] Assignee: Kanto Kagaku Kabushiki Kaisha, Tokyo, Japan

[21] Appl. No.: 713,007

[22] Filed: Jun. 10, 1991

Related U.S. Application Data

[63] Continuation of Ser. No. 121,793, Nov. 17, 1987, abandoned.

[30] Foreign Application Priority Data

Nov. 17, 1986 [JP] Japan ................. 61-271775

[51] Int. Cl.$^5$ .................... C12Q 1/40; C12Q 1/34; C12N 9/99
[52] U.S. Cl. .......................... 435/22; 435/18; 435/202; 435/204; 435/183; 435/184; 435/810
[58] Field of Search ............... 435/18, 22, 202, 204, 435/184, 183, 810

[56] References Cited

U.S. PATENT DOCUMENTS

| | | | |
|---|---|---|---|
| 4,472,489 | 9/1984 | McCroskey | 435/21 |
| 4,698,300 | 10/1987 | Henkel et al. | 435/18 |

FOREIGN PATENT DOCUMENTS

| | | | |
|---|---|---|---|
| 0199363 | 10/1986 | European Pat. Off. | 435/26 |
| 0207493 | 1/1987 | European Pat. Off. | 435/26 |
| 0259521 | 2/1988 | European Pat. Off. | 435/22 |
| 0275398 | 7/1988 | European Pat. Off. | |
| 3323245 | 10/1985 | Fed. Rep. of Germany | |
| 3614470 | 11/1986 | Fed. Rep. of Germany | |
| 0078994 | 5/1985 | Japan | 435/22 |
| 0237998 | 10/1985 | Japan | 435/22 |
| 2138199 | 6/1987 | Japan | 435/22 |

OTHER PUBLICATIONS

Dolabdjian, B., et al., Chemical Abstracts vol. 101, No. 5, abstract No. 34892m (1984).
Henkel, E., et al., Chemical Abstracts, vol. 102, No. 13, abstract No. 108927w (1985).
Nat. Bur. Stand. (Nov. 79) U.S. Dept. of Commerce (NTIS) PB80-110117 NBS Spec. Pub. 260-67.
Oesch et al. (1986) *Clin. Chem.* 32(8) 1448-1459.
Schales et al. (1941) J. Biol. Chem. 148:879-884.
J. Sendroy (1942) *J. Biol. Chem.*, 142:171-173.
Zall et al. (1956) *Anal. Chem.* 28:1665-1668.
Levitzhe et al, "The Allosteric Activation of Mammalian δ-Amylase by Chloride", pp. 171-180, 1974.
Bergmeyer, "Methods of Enzymatic Analysis", 3rd Edition, vol. IV, pp. 157-160, 1984.
Tietz, "Textbook of Clinical Chemistry", 1986, p. 729.

*Primary Examiner*—David Saunders
*Assistant Examiner*—Toni R. Scheiner
*Attorney, Agent, or Firm*—Birch, Stewart, Kolasch & Birch

[57] ABSTRACT

Quantitative assay and reagent for the determination of chlorine ion in body fluid. Body fluid is contacted with a reagent which includes deactivated α-amylase, a compound capable of chelating calcium ion, a calcium chelate compound, and an α-amylase activity-measuring substance; the amount of α-amylase activity is proportional to the amount of chlorine ion present in the body fluid. The assay is suitable for automation.

18 Claims, 2 Drawing Sheets

REAGENT FOR THE DETERMINATION OF CHLORINE ION

This application is a continuation of application Ser. No. 07/121,793 filed on Nov. 17, 1987, now abandoned, the entire contents of which are incorporated herein by reference.

BACKGROUND OF THE INVENTION

1. Field of the Invention

The present invention relates to a reagent which is effective in the determination of the presence of the chlorine ion in a substance and thus the reagent is effectively utilizable in the fields of analytical chemistry and diagnosis. More particularly, the present invention relates to a reagent for the determination of the chlorine ion, which utilizes the nature of α-amylase which is convertible from its deactivated from into its active form in the presence of the chlorine (chloride) ion.

2. Description of the Prior Art

In the field of chemistry, a great number of reports have been submitted hitherto over a century with respect to the analysis of chlorine, including a primitive routine method for the determination of the presence of the chlorine ion utilizing a soluble silver salt and the use of tolidine for the colorimetric test of free chlorine. Recently, determination of the chlorine ion is utilized in a wide variety of fields, including the precise chemical analysis and diagnosis in medical fields. Especially, determination of the chlorine ion in serum is clinically important in grasping the metabolic function of electrolytes in the living body. Methods for the determination of the chlorine ion in samples, now widely used in clinical laboratories utilize either (A) the electric methods, such as coulometric titration [velapoldi R A, Paule R C, Schaffer R et al. "A reference method for the determination of chloride in serum" Nat. Bur. Stand. (U.S.) Special Publication 260-67 (1979)] and the selective electrode method [Oesch U, Ammann D, Simon W. "Ion-selective membrane electrodes for clinical use" Clin. Chem. 1986 (32) 1448-1459], wherein the concentration of chlorine ion is measured as changes in electric signals are noted; or (B) the chemical methods, such as colorimetry [Schales O, Schales S S. "A simple and accurate method for the determination of chloride in biological fluids" J. Biol. Chem. 1941, 140, 879; Sendroy J. "Note on the Photoelectric microdetermination of chloride in biological fluids" J. Biol. Chem. 1942 142, 171-173; Zall D M, Fisher D, Garner M O. "Photometric determination of chlorides in water" Anal. Chem. 1956, (28) 1665-1668], wherein the concentration of the chlorine ion is measured according to changes in color density. Among these conventional methods for the determination of the chlorine ion, the coulometric titration method, usually employed in a manual or semi-automatic method, is considered to be the most reliable but requires time for titration. This method can hardly be set in an automatic analytical system. The ion selective electrode method involves some maintenance problem because of its silver electrodes and also fails to meet the requisites for being used in an automatic analytical system.

As a simple method for the determination of the chlorine ion, the colorimetry method is recommended since the measuring operation can be carried out with a simple device. The typical colorimetric methods quoted above are based on the principle that thiocyanate ion formed by the reaction between mercuric thiocyanate (rhodanide) and the chlorine ion forms a complex with ferric ion and gives a characteristic red orange color effective for colorimetry. The red orange color becomes deeper as the concentration of the chlorine ion becomes higher. However, particular attention has be to paid in this colorimetric method for handling chemicals for analysis because the chemicals contain the harmful mercuric ions and the thiocyanate ions. Thus, the waste solution or residue from the apparatus used in this method causes serious environmental pollution. Special devices and treatments are therefore necessary for the treatment of such waste solution and residue, thus making this colorimetric method practically less attractive.

On the other hand, it is desirable that the method for the determination of the chlorine ion can be carried out with a spectrophotometer widely employed in laboratories. Recently, it is highly desired to assemble the device for the determination of the chlorine ion in an automatic analytical system.

Under the above mentioned circumstances, there is a great demand for developing a new type method or device for the determination of the chlorine ion in a simple and precise manner using a conventional measuring device and applicable to an automatic analytical system without any problem of environmental pollution as seen in the prior art colorimetric methods.

BRIEF SUMMARY OF THE INVENTION

Accordingly, it is an object of the present invention to provide a new type reagent for the indirect determination of the chlorine ion by utilizing the enzymatic assay of α-amylase.

It is another object of the present invention to provide a reagent for the determination of the chlorine ion in a simple manner without being concerned with environmental pollution when using the reagent.

It is still another object of the present invention to provide a reagent for the determination of the chlorine ion which is utilizable in any type of spectrophotometer for general use and as an automatic analytical system for clinical use.

Other and further objects, features and advantages of the present invention will be apparent more fully from the following description.

As a result of extensive research made by the present inventors to develop a new type reagent for the determination of the chlorine ion, it has now been surprisingly found that deactivated α-amylase (referred to hereinafter simply as the deactivated AMY) is converted into the active form combined with calcium in the presence of the chlorine ion whereby the quantity of the active form of α-amylase is exactly proportional to the concentration of the chlorine ion at a certain concentration and that the concentration of the chlorine ion can be measured by the enzymatic determination of active α-amylase. The present invention has been accomplished on the basis of the above finding.

In accordance with the present invention, there is provided a reagent for the determination of the chlorine ion which comprises a compound capable of forming a chelate with the calcium ion, deactivated α-amylase, a calcium chelate compound and an α-amylase activity-measuring substance.

The present invention has various features when compared with the conventional colorimetry or coulometric titration, methods, that is, the indirect determination of the chlorine ion utilizing the reagent of the present invention can be considered an enzymatic assay of the chlorine ion based on the determination of α-amylase activity which depends on the quantity of chlorine ion.

DETAILED DESCRIPTION OF THE INVENTION

Figure 1:
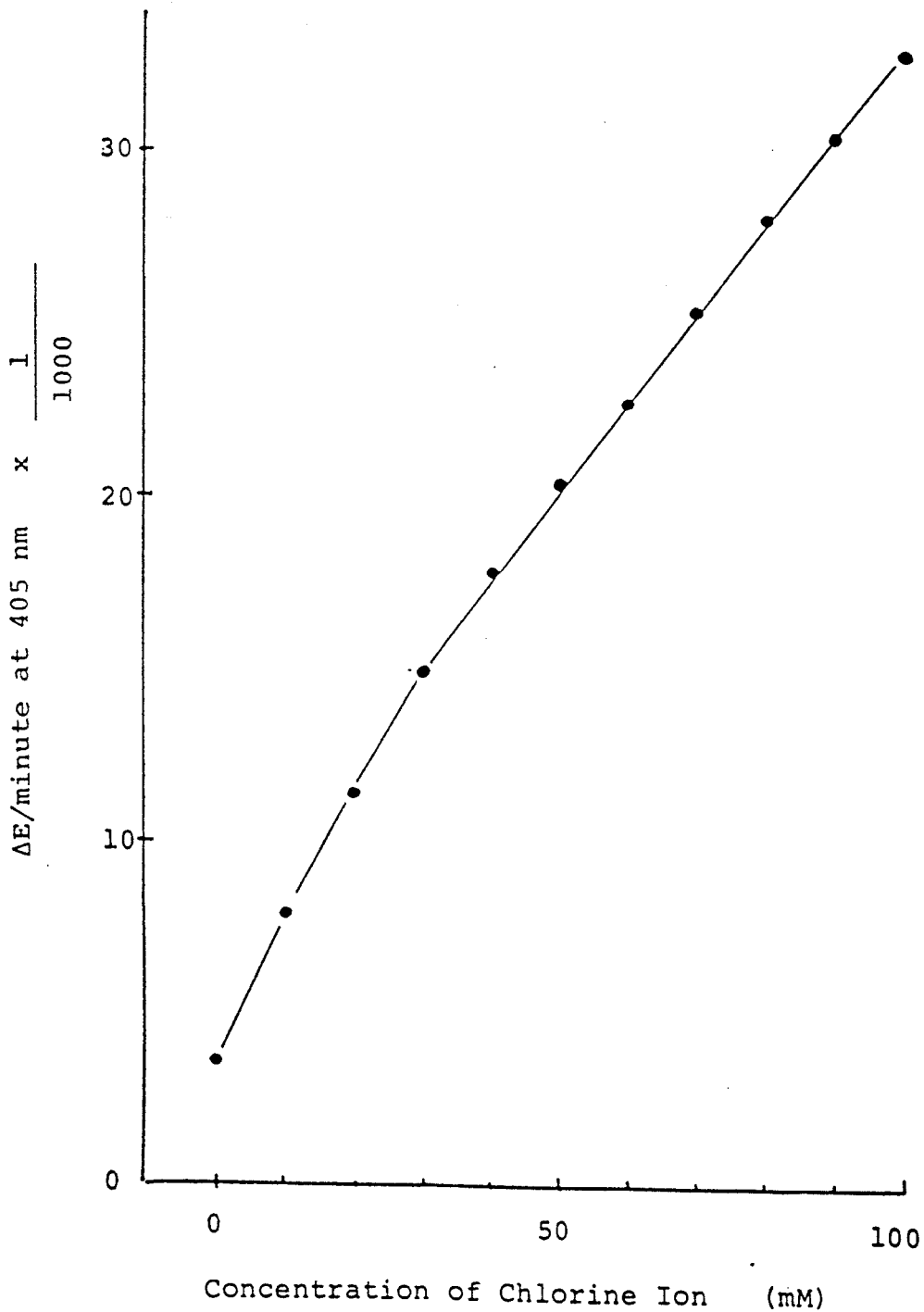
FIG. 1 is a graph showing a calibration curve prepared according to Example 1-(2) wherein the abscissa stands for the concentration of the chlorine ion in terms of m-Mol (mM) and the ordinate stands for the increase in absorbance (E/min) at 405 nm.

It is known that α-amylase (referred to hereinafter simply as AMY) exists usually in a state coupled with the calcium ion (active form). (See, for example, "Amylase" compiled by Michinori Nakamura and published on January 1986 by Gakkai Shuppan Center, Japan.) This α-amylase in active form will be referred to hereinafter as the active AMY. However, this active AMY is converted in the majority of cases into the deactivated form while releasing the calcium ion in the presence of a compound capable of forming a chelate with the calcium ion (referred to hereinafter simply as the calcium chelator) such as ethylenediaminetetraacetic acid (EDTA) having a high concentration. It is also known that when this deactivated AMY is reacted with the chlorine ion at a high concentration (e.g. 10 mM), the deactivated AMY is again coupled with the calcium ion to form active AMY (A. Levitzki and M. L. Steer, Eur. J. Biochem. 41, p. 171, 1974).

According to the present inventor's discovery, that the quantity of the active AMY is exactly proportional to the concentration of chlorine ion within a certain range, the determination of chlorine ion can be attained in the present invention indirectly by an enzymatic assay of the active AMY in the following new manner: In the first step, a sample containing chlorine ion to be measured is mixed with the deactivated AMY whereby the deactivated AMY is converted into the active AMY only in a quantity corresponding to the concentration of chlorine ion existing in the sample, and in the second step, the quantity of the active AMY is measured by an AMY activity-measuring substance. The determination of chlorine ion can thus be made indirectly by calculating the quantity of chlorine ion in the sample from the quantity of the measured active AMY in a proportional relationship.

The reagent of the present invention contains, in addition to the deactivated AMY, the calcium chelator, the calcium chelate compound and the AMY activity-measuring substance.

Illustrative of the calcium chelator are, for example, ethylenediaminetetraacetic acid (EDTA), trans-1,2-cyclohexanediamine-N,N,N',N'-tetraacetic acid, glycoletherdiaminetetraacetic acid, iminotetraacetic acid, diaminopropanetetraacetic acid. The use of EDTA is preferable.

The calcium chelate compound is in principle a chelate of the above calcium chelator with calcium ion. Thus, examples of the calcium chelate compound include calcium ethylenediaminetetraacetate (Ca-EDTA), calcium trans-1,2-cyclohexanediamine-N,N,N',N'-tetraacetate, calcium iminotetraacetate and calcium diaminopropanetetraacetate. The use of Ca-EDTA is preferable.

Any of the known α-amylase activity-measuring substances can be used as the AMY activity-measuring substance used in the present invention. A substance comprised of (a) a substrate of AMY coupling a colorant such as 4-nitrophenol or 2-chloro-4-nitrophenol to an oligosaccharide and (b) a coupled enzyme of α-glucosidase and a combination of α- and β-glucosidases, which can hydrolyze an intermediate product formed by hydrolysis of the substrate by the action of α-amylase, such as 4-nitrophenyl-α-D-maltose, 4-nitrophenyl-α-D-maltotriose, 2-chloro-4-nitrophenyl-β-D-maltose and 2-chloro-4-nitrophenyl-β-D-maltotriose, to the final product, i.e. 4-nitrophenol or 2-chloro-4-nitrophenol, is desirably used in the present invention. Illustrative of the α-amylase activity-measuring substance are, for example, a substance comprised of 4-nitrophenyl-α-D-maltopentaoside as substrate and α-glucosidase as coupled enzyme, a substance comprised of 2-chloro-4-nitrophenyl-β-D-maltopentaoside as substrate and α-glucosidase and β-glucosidase as coupled enzyme, a substance comprised of 4-nitrophenyl-α-D-maltoheptaoside as substrate and α-glucosidase as coupled enzyme, and a substance comprised of 2-chloro-4-nitrophenyl-β-D-maltoheptaoside as substrate and α-glucosidase and β-glucosidase as coupled enzyme.

The reason why the calcium chelator has to be present in the reagent of this invention is to stabilize the deactivated AMY used as the essential component in the reagent. As the calcium chelate compound is contained in the reagent of this invention, a very small portion of the deactivated AMY is supplied with calcium ion and is converted in the reagent into the active AMY even in the absence of chlorine ion. Practically, this phenomenon is reflected as a blank reagent (blank reaction) in the data obtained and apparently causes inaccuracy of the measurement. In the absence of chlorine ion, the existence of the calcium chelater effectively inhibits the reverse reaction of the deactivated AMY to the activated AMY and thus prevents the above mentioned undesirable phenomenon.

No special limitation exists in the proportion of the components used in the reagent. The quantity of the deactivated AMY is preferably larger than the corresponding quantity of the chlorine ion to be measured.

As the measurement of the AMY activity is made by an enzymatic reaction, the pH value of the reagent is preferably adjusted to an optimum value for the enzymatic reaction by using a buffer substance. Any of the conventional buffer substances can be used for this purpose. Examples of such buffer substance include phosphate buffer, tris-HCl and citrate buffer.

Using the reagent of the present invention, the determination of the chlorine ion is carried out in the following manner: The reagent of the present invention is mixed with a series of test samples containing given gradient concentrations of chlorine ion. The quantity of the active AMY in proportion to the concentration of chlorine ion is measured for each sample as AMY activity. A calibration curve is then prepared in a graph on the basis of the relation between the AMY activity and the concentration of chlorine ion. Next, the reagent of this invention is used for a sample containing an unknown concentration of chlorine ion. Using the calibration curve, the concentration of chlorine ion can easily be obtained.

The concentration of chlorine ion within a range of about 10-3000 mM in a sample can be measured with the reagent of this invention. This range fully covers the concentration of chlorine ion in serum usually within a range of 70-130 mM.

According to the present invention, the determination of chlorine ion can be carried out using any type of spectrophotometer widely available in chemical and clinical laboratories. The reagent of this invention can be utilized in an automatic analytical system for serum recently installed in many clinical laboratories. In addition, the reagent of this invention is free from any harmful substance such as mercuric ion or thiocyanate ion. Thus, no particular attention is necessary for the treatment of waste liquid from the assay unlike the conventional colorimetry.

In addition to ordinary chemical samples containing chlorides, various kinds of biological and clinical samples such as serum, plasma, urine and the like can be used for the determination of the chlorine ion as a sign of metabolic function of electrolytes. Thus, the reagent of the present invention finds a wide application in various fields of industry where determination of the chlorine ion is necessary.

The present invention will now be illustrated in more detail by way of Examples wherein Example 1 illustrates the method for preparing a calibration curve, Example 2 illustrates the determination of chlorine ion in human serum with a spectrophotometer and Example 3 illustrates application of the reagent of the present invention to an automatic analytical system for determination of chlorine ion in human sera.

EXAMPLE 1

Preparation of the reagent and a calibration curve

In this example, $\alpha$-glucosidase, $\beta$-glucosidase and 2-chloro-4-nitrophenyl-$\beta$-D-maltoheptaoside were used as the $\alpha$-amylase measuring reagent in such manner that the $\alpha$-glucosidase and $\beta$-glucosidase were used as components of the ingredient (B) in consideration of their stability with the lapse of time, and that the 2-chloro-4-nitrophenyl-$\beta$-D-maltoheptaoside was used as a component of the ingredient (C).

(1) Preparation of the reagent

Each ingredient of the reagent was prepared in the following manner:

(A) Preparation of the deactivated AMY $\alpha$-Amylase extracted from pig pancreas was dialyzed for 24 hours in a 0.1M phosphate buffer solution (pH 7.0) containing 0.01M EDTA to prepare a deactivated AMY.

(B) Preparation of a solution containing a chelate compound containing calcium ion and a calcium chelator To 100 ml of a 0.1M phosphate buffer solution (pH 6.2) were added 15 mg of calcium ethylenediaminetetraacetate as the calcium chelate compound and 1.7 g of disodium ethylenediaminetetraacetate as the calcium chelator. After adding to the buffer solution a 5% aqueous solution of sodium hydroxide to adjust the pH value of the buffer solution to 6.9, 11 KU of $\alpha$-glucosidase and 300 U of $\beta$-glucosidase (enzymes) were added to the solution.

To 100 ml of the resultant solution was added 500 U of the deactivated AMY prepared in the foregoing step (A) to prepare Solution R1.

(C) Preparation of the $\alpha$-amylase activity measuring reagent 1.0 Gram of 2-chloro-4-nitrophenyl-$\beta$-D-maltoheptaoside (substrate) was dissolved in 100 ml of distilled water to prepare Solution R2.

(2) Preparation of a calibration curve

First of all, a series of edible salt solutions of gradient concentration were prepared as samples each containing a given concentration of chlorine (chloride) ion. Namely, aqueous solutions of sodium chloride each containing 0, 10, 20, 30, 40, 50, 60, 70, 80, 90 and 100 mM of sodium chloride were prepared as samples. 0.1 Milliliter of each sample was added to 2.0 ml of the Solution R1 and then 0.5 ml of the Solution R2 was added to each sample. Using a spectrophotometer (Model 3200, Hitachi), increase in absorbance of the sample with the lapse of time ($\Delta E$/min) at a wave length of 405 nm were measured at 37° C.

Using an ordinate to express $\Delta E$/min and an abscissa to express the concentration of chlorine ion in a graph, the measured values are plotted in the graph to prepare a calibration curve, which is shown in FIG. 1. In this calibration curve, the concentration of chlorine ion is exactly proportional to the measured $\Delta E$/min value at a chlorine ion concentration of at least 30 mM. Thus, it is possible to determine chlorine ion exactly with this calibration curve which is rather linear at a chlorine ion concentration above 30 mM.

EXAMPLE 2

Determination of chlorine ion in human sera

Using a human serum as a sample, increase in absorbance at 405 nm with the lapse of time ($\Delta E$/min) of the sample was measured according to the method (2) described in Example 1 wherein a combination of Solutions R1 and R2 is used as the reagent for measuring the active $\alpha$-AMY. The concentration of chlorine ion in the serum sample (S-1) in terms of mM was then calculated according to the calibration curve prepared in Example 1(2). In the same manner using the same serum sample, the concentration of chlorine ion contained therein was measured repeatedly for 19 times under the same conditions, and the 20 values (S-1 to S-20) measured were statistically treated to calculate their mean value ($\bar{x}$), standard deviation (SD) and coefficient value (CV). Table 1 below shows the calculated values for these samples.

TABLE 1

| Sample | Tests for coefficient value (CV) | | |
|---|---|---|---|
| | Cl concentration | Sample | Cl concentration |
| S-1 | 100 mM | S-11 | 100 mM |
| S-2 | 100 mM | S-12 | 101 mM |
| S-3 | 99 mM | S-13 | 101 mM |
| S-4 | 100 mM | S-14 | 101 mM |
| S-5 | 98 mM | S-15 | 103 mM |
| S-6 | 100 mM | S-16 | 101 mM |
| S-7 | 99 mM | S-17 | 102 mM |
| S-8 | 100 mM | S-18 | 100 mM |
| S-9 | 99 mM | S-19 | 100 mM |
| S-10 | 102 mM | S-20 | 101 mM |

$\bar{x}$: 100.35 mM; SD: 1.18 mM; CV: 1.17%

EXAMPLE 3

A reagent for determination of chlorine ion for use in an automatic analytical system This reagent consists of three ingredients which can be prepared in the following manner:

(A) Lyophilized Ingredient 1 (Powdery Ingredient 1)

In 50 ml of purified water was dissolved 77 mg of glutathion as a stabilizer for the deactivated AMY. After adjusting the pH value of the solution to 7.0 with a 5(w/v) % aqueous solution of sodium hydroxide, 11 KU of α-glucosidase, 300 U of β-glucosidase and 2000 U of the deactivated AMY prepared in accordance with the method described in Example 1-(1)-(A), were added to the solution. The mixture was then subjected to lyphilization to prepare Lyphilized (Powdery) Ingredient 1.

(B) Lyophilized Ingredient 2 (Powdery Ingredient 2)

In 10 ml of purified water were dissolved 0.25 g of 2-chloro-4-nitrophenyl-β-D-maltoheptaoside and 1.25 g of maltopentose as a sensibility-adjusting agent. The liquid mixture was then subjected to lyophilization to prepare Lypophilized (Powdery) Ingredient 2.

(C) Buffer Solution (Liquid Ingredient 3)

In about 900 ml of purified water were dissolved 17.4 g of potassium dihydrogen phosphate, 13.6 g of tetrasodium ethylenediaminetetraacetate tetrahydrate, 0.3 g of calcium ethylenediaminetetraacetate dihydrate and 5 g of thiourea. After adjusting the pH value of the solution to 7.0 with orthophosphoric acid, purified water was added to the solution to make the whole volume to 1 liter.

On actual use of this reagent, the lyophilized Reagent 1 is dissolved in 100 ml of the Buffer Solution of prepare Reagent 1, while the Lyophilized Ingredient 2 is dissolved in 50 ml of the Buffer Solution to prepare Reagent 2. A combination of the above mentioned Reagents 1 and 2 is set in any type of the automatic analytical system, for example, Hitachi 705 analytical system. In this case, the final concentration of the individual components used in an automatic analytical system are as shown in Table 2 with the proviso that the Reagent 1 and the Reagent 2 are used in a volume ratio of 4:1.

Figure 2:
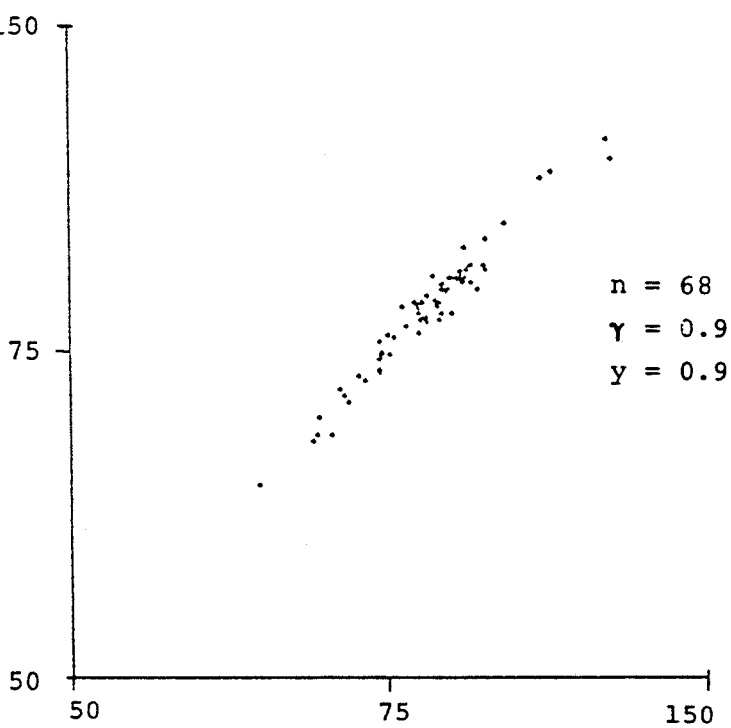
FIG. 2 is a graph showing the correlation in the measurement of the concentration of chlorine ion between the present invention and the coulometric titration method, wherein the abscissa stands for the value measured according to the coulometric titrator and the ordinate for the value measured according to Hitachi 705 automatic analytical system using the reagent prepared in Example 3 and 68 human serum samples.

Using the reagent for determination of chlorine ion prepared in Example 3 for Hitachi 705 automatic analytical system, the sensitivity and the correlation with the coulometric titrator were examined. As a result of the test, the variation speed of absorbance was 0.160/min for chlorine ion at a concentration of 100 mM/liter. As shown in FIG. 2, a great correlation is observed, indicating ($\gamma$)=0.9774 and aregression line of $y=0.962343x+3.447$.

TABLE 2

The final concentration of the individual components in case of using the reagent prepared in Example 3 for the automatic analytical system

| | |
|---|---|
| α-glucosidase | 88 KU/liter |
| β-glucosidase | 2.4 KU/liter |
| deactivated AMY | 16 KU/liter |
| ethylenediaminetetraacetic acid | 30 mM |
| calcium ethylenediaminetetraacetate | 0.75 mM |
| thiourea | 0.5 (w/v) % |
| glutathion | 2.0 mM |
| 2-chloro-4-nitorphenyl-β-D-maltoheptaoside | 0.75 mM |
| maltopentaose | 0.5 (w/v) % |
| a phosphate buffer solution (pH 7.0) | 0.15 M. |

On the preparation of a reagent for an automatic analytical system, it is desirable to stabilize the ingredients of the reagent and adapt the sensitivity of the reagent to the system. In this Example, the deactivated AMY, α-glucosidase and β-glucosidase were lyophilized together with glutathion as an enzyme stabilizer to prepare Powdery Ingredient 1 wherein the stability of the components is maintained. Further, maltopantaose was added together with 2-chloro-4-nitrophenyl-β-D-maltoheptaoside to the lyophilized Powdery Ingredient 2 for the purpose of adjusting sensitivity.

In this Example, 68 samples of human sera were used to check the correlation.

It is understood that the preceding representative examples may be varied within the scope of the present specification both as to components and proportions, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A method for determining the concentration of chloride ions in a bodily fluid sample, comprising:
   (a) contacting a bodily fluid sample suspected of containing chloride ions with a reagent which comprises a compound capable of forming a chelate with a calcium ion, deactivated α-amylase, a calcium chelate compound, and an α-amylase activity-measuring substance;
   (b) determining the quantity of active α-amylase formed due to the presence of chloride ions in said bodily fluid sample, which is directly proportional to the amount of chloride ions present in said bodily fluid sample; and
   (c) determining the quantity of said chloride ions from the quantity of said active α-amylase by referring to a calibration curve.

2. The method according to claim 1, wherein said compound capable of forming a chelate with a calcium ion is a member selected from the group consisting of ethylenediaminetetraacetic acid, trans-1, 2-cyclohexanediamine-N,N,N',N'-tetraacetic acid, glycoletherdiaminetetraacetic acid, iminotetraacetic acid and diaminopropanetetraacetic acid.

3. The method according to claim 2, wherein said compound capable of forming a chelate with a calcium ion is ethylenediaminetetraacetic acid.

4. The method according to claim 1, wherein said calcium chelate compound is a member selected from the group consisting of calcium ethylenediaminetetraacetate, calcium trans-1,2-cyclohexanediamine-N,N,N',N'-tetraacetate, calcium iminotetraacetate, and calcium diaminopropanetetraacetate.

5. The method according to claim 4, wherein said calcium chelate compound is calcium ethylenediaminetetraacetate.

6. The method according to claim 1, wherein said α-amylase activity-measuring substance is a member selected from the group consisting of 4-nitrophenyl-α-D-maltopentaoside and α-glucosidase, 2-chloro-4-nitrophenyl-β-D-maltopentaoside and α-glucosidase and β-glucosidase, 4-nitrophenyl-α-D-maltoheptaoside and α-glucosidase, and 2-chloro-4-nitrophenyl-β-D-maltoheptaoside and α-glucosidase and β-glucosidase.

7. The method according to claim 6, wherein said α-amylase activity-measuring substance is 2-chloro-4-nitrophenyl-β-D-maltoheptaoside and α-glucosidase and β-glucosidase.

8. A method according to claim 1, comprising:
(a) contacting a bodily fluid sample suspected of containing chloride ions with a reagent which comprises ethylenediaminetetraacetic acid, deactivated α-amylase, calcium ethylenediaminetetraacetate, and 2-chloro-4-nitrophenyl-β-D-maltoheptaoside and α-glucosidase and β-glucosidase;
(b) determining the quantity of active α-amylase formed due to the presence of chloride ions in said bodily fluid sample, which is directly proportional to the amount of chloride ions present in said bodily fluid sample; and
(c) determining the quantity of said chloride ions from the quantity of said active α-amylase by referring to a calibration curve.

9. The method according to claim 1, wherein said bodily fluid sample is a sample of serum, plasma, or urine.

10. A reagent for use in determining the concentration of chloride ions in a fluid sample, comprising a compound capable of forming a chelate with a calcium ion, deactivated α-amylase, a calcium chelate compound, and an α-amylase activity-measuring substance.

11. The reagent according to claim 10, wherein said compound capable of forming a chelate with a calcium ion is a member selected from the group consisting of ethylenediaminetetraacetic acid, trans-1,2-cyclohexanediamine-N,N,N',N'-tetraacetic acid, glycoletherdiaminetetraacetic acid, iminotetraacetic acid, and diaminopropanetetraacetic acid.

12. The reagent according to claim 11, wherein said compound capable of forming a chelate with a calcium ion is ethylenediaminetetraacetic acid.

13. The reagent according to claim 10, wherein said calcium chelate compound is a member selected from the group consisting of calcium ethylenediaminetetraacetate, calcium trans-1,2-cyclohexanediamine-N,N,N',N'-tetraacetate, calcium iminotetraacetate, and calcium diaminopropanetetraacetate.

14. The reagent according to claim 13, wherein said calcium chelate compound is calcium ethylenediaminetetraacetate.

15. The reagent according to claim 10, wherein said α-amylase activity-measuring substance is a member selected from the group consisting of 4-nitrophenyl-α-D-maltopentaoside and α-glucosidase 2-chloro-4-nitrophenyl-β-D-maltopentaoside and α-glucosidase and β-glucosidase, and 4-nitrophenyl-α-D-maltoheptaoside and α-glucosidase, and 2-chloro-4-nitrophenyl-β-D-maltoheptaoside and α-glucosidase and β-glucosidase.

16. The reagent according to claim 15, wherein said α-amylase activity-measuring substance is 2-chloro-4-nitrophenyl-β-D-maltoheptaoside and α-glucosidase and β-glucosidase.

17. The reagent according to claim 10, comprising ethylenediaminetetraacetic acid, deactivated α-amylase, calcium ethylenediaminetetrraacetate, and 2-chloro-4-nitrophenyl-β-D-maltoheptaoside and α-glucosidase and β-glucosidase.

18. A method of using said reagent according to claim 10 for determining the concentration of chloride ions contained in a sample of bodily fluid for diagnostic purposes, comprising adding to said bodily fluid sample said reagent of claim 10, and measuring the amount of active α-amylase formed and, correspondingly, the amount of chloride ions present in said bodily fluid sample.

* * * * *